United States Patent [19]
Earley et al.

[11] Patent Number: 5,428,004
[45] Date of Patent: Jun. 27, 1995

[54] COMPOUNDS USEFUL AS DUAL ANTAGONISTS OF PLATELET ACTIVATING FACTOR AND LEUKOTRIENE $D_4$

[75] Inventors: James V. Earley, Cedar Grove; Norman W. Gilman, Wayne; Perry Rosen, North Caldwell, all of N.J.

[73] Assignee: Hoffmann-La Roche Inc., Nutley, N.J.

[21] Appl. No.: 164,084

[22] Filed: Dec. 8, 1993

Related U.S. Application Data

[62] Division of Ser. No. 993,227, Dec. 18, 1992, Pat. No. 5,302,590.

[51] Int. Cl.⁶ .............................................. C07D 495/14
[52] U.S. Cl. ........................................................ 540/560
[58] Field of Search ........................................... 540/560

[56] References Cited
U.S. PATENT DOCUMENTS

| | | | |
|---|---|---|---|
| 4,959,361 | 9/1990 | Walser | 514/220 |
| 5,001,140 | 3/1991 | Field et al. | 514/365 |
| 5,302,590 | 4/1994 | Earley et al. | 514/220 |

Primary Examiner—John M. Ford
Attorney, Agent, or Firm—George M. Gould; William H. Epstein; Catherine A. Picut

[57] ABSTRACT

The invention relates to compounds of the formula

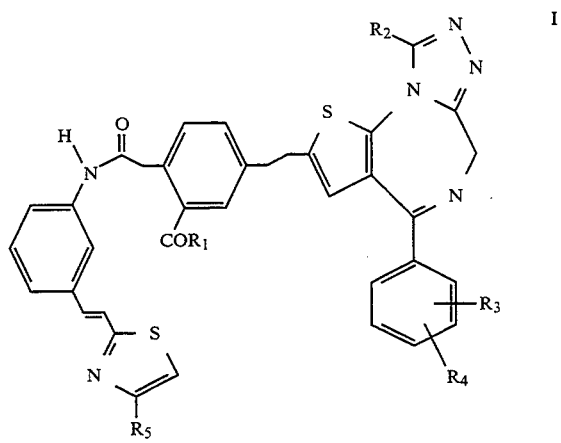

wherein $R_1$ is $OR_6$ or $NHR_7$, $R_6$ and $R_7$, which may be, the same or different, are hydrogen, lower alkyl, lower alkenyl, cycloalkyl having between 3 to 6 carbon atoms or phenyl, $R_2$ is lower alkyl, lower alkoxy or trifluoromethyl, $R_3$ and $R_4$, independently, are hydrogen, chlorine, fluorine, lower alkyl or lower alkoxy, and $R_5$ is lower alkyl or cycloalkyl having between 3 to 6 carbon atoms, and when at least one asymetric carbon is present, enantiomers, and racemates thereof, and pharmaceutically acceptable salts thereof.

The compounds of formula I and pharmaceutically acceptable salts thereof are useful as bronchopulmonary agents for example in the relief of asthma and allergic reactions.

In another aspect, the invention relates to pharmaceutical compositions, methods of using the compound of formula I and intermediates.

6 Claims, No Drawings

COMPOUNDS USEFUL AS DUAL ANTAGONISTS OF PLATELET ACTIVATING FACTOR AND LEUKOTRIENE D4

This is a division of application Ser. No. 07/993,227, filed Dec. 18, 1992, now U.S. Pat. No. 5,302,590.

SUMMARY OF THE INVENTION

The invention relates to compounds of the formula

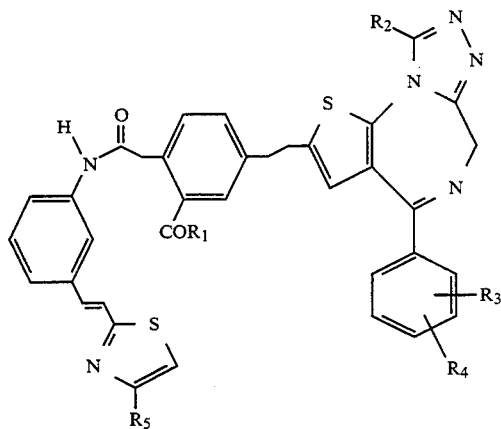

wherein $R_1$ is $OR_6$ or $NHR_7$, $R_6$ and $R_7$, which may be the same or different, are hydrogen, lower alkyl, lower alkenyl cycloalkyl having between 3 to 6 carbon atoms or phenyl, $R_2$ is lower alkyl, lower alkoxy or trifluoro methyl, $R_3$ and $R_4$, independently, are hydrogen, chlorine, fluorine, lower alkyl or lower alkoxy, and $R_5$ is lower alkyl or cycloalkyl having between 3 to 6 carbon atoms and when at least one asymetric carbon is present, enantiomers, diastereomers and racemates thereof, and pharmaceutically acceptable salts thereof.

The compounds of formula I and pharmaceutically acceptable salts thereof are useful as bronchopulmonary agents for example in the relief of asthma and allergic reactions.

In another aspect, the invention relates to pharmaceutical compositions, methods of using the compound of formula I and intermediates.

DESCRIPTION OF THE INVENTION

The invention relates to compounds of the formula

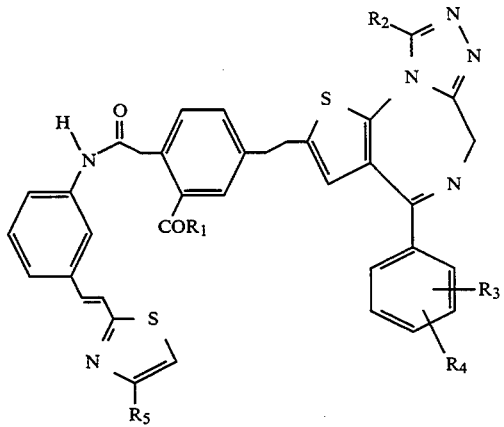

wherein $R_1$ is $OR_6$ or $NHR_7$, $R_6$ and $R_7$, which may be the same or different, are hydrogen, lower alkyl, lower alkenyl cycloalkyl having between 3 to 6 carbon atoms or phenyl, $R_2$ is lower alkyl, lower alkoxy or trifluoro methyl, $R_3$ and $R_4$, independently, are hydrogen, chlorine, fluorine, lower alkyl or lower alkoxy, and $R_5$ is lower alkyl or cycloalkyl having between 3 to 6 carbon atoms and when at least one asymetric carbon is present, enantiomers, diastereomers and racemates thereof, and pharmaceutically acceptable salts thereof.

The compounds of formula I and pharmaceutically acceptable salts thereof are useful as bronchopulmonary agents for example in the relief of asthma and allergic reactions.

In another aspect, the invention relates to pharmaceutical compositions, methods of using the compound of formula I and intermediates.

As used herein, the term "lower alkyl" preferably denotes a straight or branched chain saturated hydrocarbon containing 1 to 7 carbon atoms, for example, methyl, ethyl, propyl, isopropyl, butyl, t-butyl, neopentyl, pentyl, hexyl, heptyl and the like. The term "lower alkenyl" denotes a straight or branched chain hydrocarbon having at least one double bond containing 3 to 7 carbon atoms, for example, propenyl, butenyl, pentenyl, hexenyl and the like. The term "lower alkoxy" denotes an alkyl ether group in which the alkyl group is as described above, for example, methoxy, ethoxy, propoxy, pentoxy and the like. The term "cycloalkyl" denotes a cyclic alkyl group of 3 to 6 carbon atoms, for example, cyclopropyl, cyclobutyl, cyclopentyl, cyclohexyl and the like. Unless otherwise indicated, halogen refers to all four forms, i.e., fluorine, chlorine, bromine and iodine.

A preferred group of the compounds of formula I are those wherein $R_2$ is lower alkyl, $R_3$ is chlorine or fluorine, $R_4$ is hydrogen and $R_5$ is cycloalkyl having between 3 to 6 carbon atoms.

A more preferred group of the compounds of formula I are those wherein $R_2$ is lower alkyl, $R_3$ is chlorine, $R_4$ is hydrogen and $R_5$ is cyclobutyl.

(E)-5-[2-[4-(2-chlorophenyl)-9-methyl-6H-thieno-[3,2f][1,2,4]triazolo[4,3-a][1,4]diazepin-2-yl]ethyl]-2-[2-[3-[2-(4cyclobutyl-2-thiazolyl)ethenyl]-phenylamino]-2-oxoethyl]-benzoic acid monohydrate.

E)-4-[2-[4-(2-chlorophenyl)-9-methyl-6H-thieno-[3,2-f][1,2,4]triazolo[4,3-a][1,4]diazepin-2-yl]ethyl]-N-[3-[2-(4-cyclobutyl-2-thiazolyl)ethenyl]phenyl- 2-[2-propenylamino)-carbonyl]benzeneacetamide.

(E)-5-[2-[4-(2-chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]-phenylamino]-2-oxoethyl]-benzoic acid ethyl ester.

(E)-5-[2-[4-(2-fluorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]-phenylamino]-2-oxoethyl]-benzoic acid monohydrate.

E )-4-[2-[4-(2-fluorophenyl)- 9-methyl-6H-thieno-[3,2-f][1,2,4]triazolo[4,3-a][1,4]diazepin-2-yl]ethyl]-N-[3-[2-(4.-cyclobutyl-2-thiazolyl)ethenyl]phenyl]-2- [2-propenylamino)-carbonyl]benzeneacetamide.

(E)-5-[2-[4-(2-fluorophenyl)-9-methyl-6H-thieno-[3,2-f[]1,2,4]triazolo[4,3-a][1,4]diazepin-2-yl]ethyl]-2-[2-[3-[2-(4-cyclobutyl-2-thiazolyl)ethenyl]-phenylamino]-2-oxoethyl]-benzoic acid ethyl ester.

The compounds of formula I can be prepared as hereinafter described in reaction Scheme 1.
Scheme I
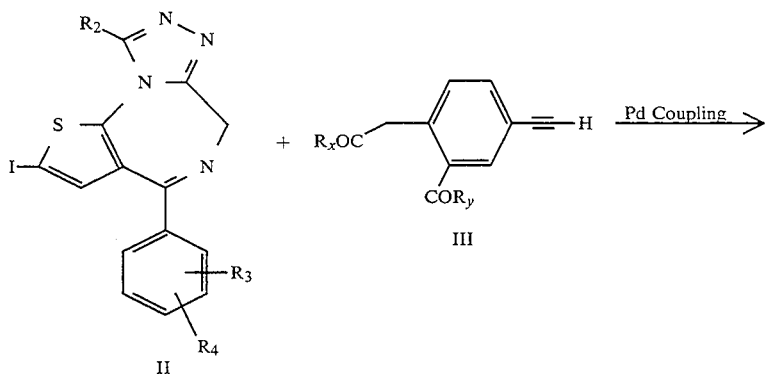
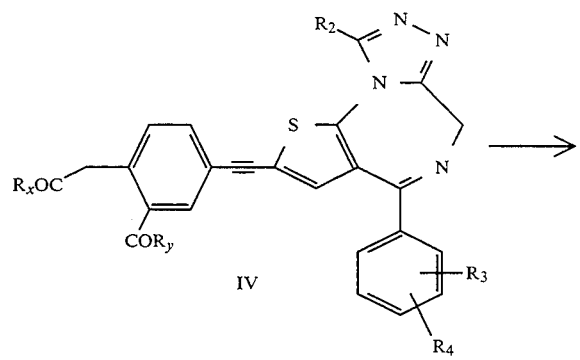
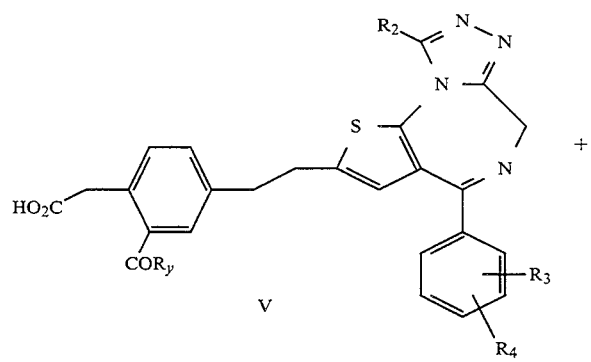

-continued

Scheme I

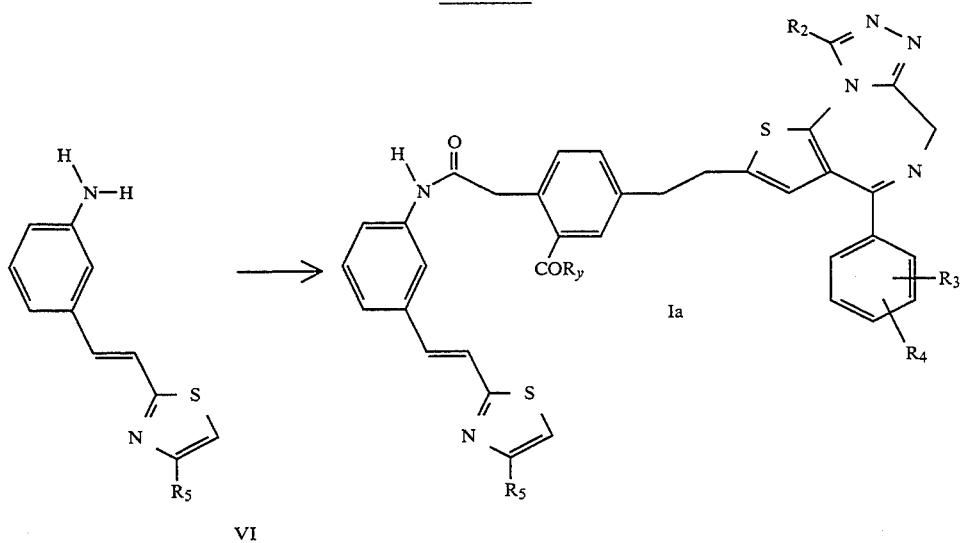

$R_x$ and $R_y$ = lower alkoxy

In reaction Scheme 1, an iodothiophene[1,4]diazepine of formula II which is a known compound or may be prepared by known methods is reacted with 4-ethynylhomophthalic acid alkyl ester of formula III in an inert solvent, preferred solvents are acetonitrile, tetrahydrofuran and dimethylformamide, at a temperature in the range from room temperature to about 100° C., in the presence of palladium catalyst, for example bis (triphenyl phosphine) palladium dichloride or diacetate, and optionally in the presence of a catalytical amount of cuprous iodide and art excess of a proton acceptor, such as, triethylamine to give a compound of formula IV.

Thereafter, the compound of formula IV is hydrogenated over a suitable catalyst such as palladium on carbon followed by partial hydrolysis through treatment with base such as dilute sodium hydroxide at a temperature between room temperature and 100° C. to give the half acid ester of formula V.

Reacting the compound of formula V with the aniline of formula VI in a suitable solvent such as a halogenated hydrocarbon in the presence of a coupling agent, such as, N-ethyl-N'-(3-dimethylaminopropyl)carbodiimide hydrochloride at a temperature in the range from room temperature to about 100° C. yields the amide ester of formula Ia.

Basic hydrolysis of the compound of formula Ia with, for example, sodium hydroxide gave the acid form of formula I, which can be convened to the amide and ester forms of formula I by the appropriate known reactions.

The invention also relates to the salts of the compounds of formula I, their enantiomers, diastereomers and racemates thereof, which salts can be prepared by the reaction of the said compounds with an appropriate acid or base having a non-toxic, pharmaceutically acceptable counter-ion.

In general, when $R_1$ is hydroxy, any base which will form a salt with a carboxylic acid and whose pharmacological properties will not cause an adverse physiological effect when ingested is considered as being within the scope of this invention. Suitable bases thus include, for example, the alkali metal and alkaline earth metal hydroxides and carbonates, ammonia, primary, secondary and tertiary amines, such as, monoalkylamines, dialkylamines, trialkylamines, nitrogen containing heterocyclic amines, for example, piperidine and the like.

The compounds of formula I can also form acid addition salts with strong inorganic or organic acids. Thus, they form pharmaceutically acceptable acid addition salts with both pharmaceutically acceptable organic and inorganic acids, for example, with hydrohalic acids, such as, hydrochloric acid hydrobromic acid, hydroiodic acid, other mineral acids, such as, sulfuric acid, phosphoric acid, perchloric acid or the like, alkyl and mono-aryl sulfonic acids such as ethanesulfonic acid, toluenesulfonic acid, benzenesulfonic acid, or the like. Non-pharmaceutically acceptable acid addition salts of a compound of formula I can be converted into pharmaceutically acceptable acid additions salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I and their pharmaceutically acceptable salts are active as inhibitors of bronochoconstriction and are therefore useful as bronchopulmonary agents, for example, in the relief of asthma and allergic reactions.

The compounds of formula I also exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

The useful dual activity of the compounds of formula I can be demonstrated by the following procedures:

LEUKOTRIENE-INDUCED BRONCHOCONSTRICTION IN GUINEA PIGS—IN VIVO LEUKOTRIENE D4 (LTD) ANTAGONIST TEST

Intravenous and Oral Testing

Male guinea pigs (Hartley strain Charles River) weighing 300–500 g were anesthetized with urethane (~2 g/kg) intraperitoneally and a polyethylene cannula was inserted into the jugular vein for intravenous drug administration. Tracheal pressure (cm of $H_2O$) was recorded from a Statham pressure transducer (P 32 AA). Propranolol was administered 5 minutes prior to challenge with LTD. Two minutes later spontaneous breathing was arrested with succinylcholine chloride (1.2 mg/kg) administered intravenously, and the animals were ventilated with a Harvard (Model #680) small animal respirator set at 40 breaths/rain and 4.0 cc stroke volume. Control vehicle or test drug was administered through the cannula into the jugular vein 1 minute before the animals were challenged intravenously with a maximum constrictory dose of LTD (25 µg/kg) given intravenously. The change in tracheal pressure was averaged for control and drug-treated animals and percent inhibition was calculated. For determination of oral activity, animals were dosed with test compound or vehicle two hours prior to challenge with LTD (25 µg/kg, i.v.).

The relative potency ($ID_{50}$ values) of test compounds administered by the intravenous and oral route was determined by administering increasing doses of test compound. For determination of the time course of inhibition for various compounds, the time between administration of compound and challenge with LTD was varied. The time course of activity was calculated as the time when inhibition decreased to 40%.

PAF Induced Bronchoconstriction Assay

Male animals (Hartlet Strain, 400–500 g were anesthetized with urethane (2 g/kg, i.p.). Each animals' trachea was cannulated and the guinea pigs were respirated using a Harvard small animal rodent respirator (3.0 cc stroke volume, 40 breaths per min.) Tracheal pressure was recorded from a cannula inserted in the trachea and connected to a Statham pressure transducer.

The jugular vein was cannulated for administering compounds. Spontaneous breathing was arrested with succinylcholine (1.2 mg/kg, i.v.) administered 2 minutes prior to intravenous injection of platelet activating factor PAF). Since propranolol has been shown to enhance bronchoconstrictor responses, all animals were pretreated five minutes prior to challenge with propranolol (0.1 mg/kg, i.v.).

For the intravenous testing, the guinea pig is given a 1-minute pretreatment with propranolol at a dose of 0.1 mg/kg intravenously. The test compound is administered with a 1 minute pretreatment prior to intravenous challenge with PAF. The animal is then challenged with a 1 µg/kg intravenous dose of PAF and the change in tracheal pressure is measured.

For the oral testing, the procedure includes a 2-hour pretreatment period with the test compound administered through an oral gavage tube. Propranolol or succinylcholine and PAF are administered intravenously, and the change in tracheal pressure measured.

The change in tracheal pressure is determined by subtracting the steady state baseline achieved after administration of succinylcholine from the peak bronchoconstriction seen after challenge with PAF. The mean is calculated for each test compound and compared to the mean of the control animals to give the percent inhibition of bronchoconstriction. The standard error is calculated as the standard error of the mean.

The results obtained are set forth in Table 1 which follows:

The compounds listed below were evaluated for antagonist activity against bronchoconstriction induced by PAF or $LTD_4$. Comparative data for a known $LTD_4$ antagonist (Compound B) and a known PAF antagonist (Compound A) are also shown. Compounds of this invention (C and D) were very potent dual acting antagonists when administered IV.

Compound A—5-{3-[4-(2-Chlorophenyl)-9-methyl-6H-thieno[3,2f][1,2,4 ]triazolo [4,3-a][1,4]diazepin-2-yl]-2-propynyl}phenanthridin-6(5H)-one Compound B—(E)-4-[3-[2-(4-Cyclobutyl-2-thiazolyl)ethenyl]phenylamino]2,2-diethyl-4-oxobutanoic acid Compound C—(E)-5-[2-[4-(2-Chlorophenyl)-9-methyl-6H-thieno-[3,2-f][1,2,4]triazolo[4,3-a][1,4 ]diazepin-2-yl]ethyl]-2-[2-[3-[2-(4-cyclobutyl-2-thiazolyl)ethenyl]phenylamino]-2-oxoethyl]-benzoic acid monohydrate Compound D—(E)-4-[2-[4-(2-Chlorophenyl)-9-methyl-6H-thieno-[3,2-f][1,2,4]triazolo[4,3-a][1,4]diazepin2-yl]ethyl]-N-[3-[2-(4-cyclobutyl-2-thiazolyl)ethenyl]phenyl]-2-[2-propenylamino)-carbonyl]benzeneacetamide.

Compound E
(E)-5 -[2-[4-(2-Chlorophenyl)-9-methyl-6H-thieno-[3,2-f][1,2,4]triazolo [4,3-a][1,4]diazepin-2-yl]ethyl]-2-[2-[3-[2-(4-cyclobutyl-2-thiazolyl)ethenyl]-phenylamino]-2-oxoethyl]-benzoic acid ethyl ester Compounds C, D and E were administered orally at a dose of 10 mg/kg.

TABLE 1

| | Antagonist Activity Against PAF and $LTD_4$ Induced Bronchoconstriction | | | |
|---|---|---|---|---|
| | PAF-induced bronchoconstriction[a] $ID_{50}$ (mg/kg) | | $LTD_4$-induced bronchoconstriction[b] $ID_{50}$ (mg/kg) | |
| compound | iv | po | iv | po |
| Compound A | 0.02 | 0.12 | Not Active | Not Active |
| Compound B | Not Active | Not Active | 0.13 | 0.12 |
| Compound C | 0.02 | 37 ± 1% | 0.01 | 48 ± 8% |
| Compound D | 0.02 | 65 ± 1% | 0.08 | 44 ± 15% |
| Compound E | 0.02 | 14 ± 9% | 46 ± 7% | Not Determined |

A compound of formula I, an enantiomer, a diastereomer or racemate thereof or a salt thereof or a composition containing a therapeutically effective amount of a compound of formula I, an enantiomer, a diastereomer or racemate thereof or a salt thereof can be administered by methods well known in the art. Thus, a compound of formula I, an enantiomer, a diastereomer or racemate thereof or a salt thereof can be administered either singly or with other pharmaceutical agents, for example, antihistamines, mediator release inhibitors, methyl xanthines, beta agonists or antiasthmatic steroids such as prednisone and prednisoline, orally, parenterally, rectally, or by inhalation, for example, in the form of an aerosol, micropulverized powder or nebulized solution. For oral administration they can be administered in the form of tablets, capsules, for example, in admixture with talc, starch, milk, sugar or other inert ingredients, that is, pharmaceutically acceptable carriers, or in the form of aqueous solutions, suspensions, elixiers or aqueous alcoholic solutions, for example, in admixture with sugar or other sweetening agents, flavoring agents, colorants, thickeners and other coventional pharmaceutical excipients. For parenteral administration, they can be administered in solutions or suspension, for example, as an aqueous or peanut oil solution or suspension using exceipients and carriers conventional for this mode of aministration. For administration as aerosols, they can be dissolved in a suitable pharmaceutically acceptable solvent, for example, ethyl alcohol or cominations of miscible solvents, and mixed with a pharmaceutically acceptable propellant. Such aerosol compositions are packaged for use in a pressurized container fitted with an aerosol valve suitable for release of the pressurized compositions. Preferably, the aerosol valve is a metered valve, that is one which on activation releases a predetermined effective dose of the aerosol composition.

In the practice of the invention, the dose of a compound of formula I or a salt thereof to be administered and the frequency of aministration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 1 mg/kg to about 100 mg/kg per day, preferably about 10 mg/kg to about 25 mg/kg either as a single dose or in divided doses.

The examples which follow further illustrate the invention. All temperatures are in degrees celsius unless otherwise stated.

EXAMPLE 1

4-[[4-(2-Chlorophenyl)-]-methyl-6H-thieno[3,2-f][1,2,4]triazolo[4,3a][1,4]diazepin-2-yl]ethynyl]-2-(ethoxycarbonyl)benzeneacetic acid diethyl ester A mixture of 2.6 g (5.8 mmol) of 8-iodo-1-methyl-6-(2-chlorophenyl)-4H-5-triazolo[3,4-c]thieno[2,3-e][1,4]diazepine, 1.9 g (7.3 mmol) of 2-ethoxycarbonyl-4-ethynyl-benzeneacetic acid diethyl ester, 125 mg of triphenylphosphine, 32 mg of cuprous iodide, 40 ml of dry DMF, and 4 mL of triethylamine was stirred under nitrogen for 20 minutes, and then 50 mg of palladium acetate was added and the reaction stirred 72 hours at room temperature. After the addition of ice water, the solids were collected by filtration, dissolved in $CH_2Cl_2$ and washed with dilute $NH_4OH$. The organic phases were dried and concentrated. The residue was triturated with ethyl acetate and filtered to remove insoluble material. The filtrates were concentrated and chromatographed over neutral alumina using first $CH_2Cl_2$, $CH_2Cl_2$ diethyl ether and finally diethyl ether as the eluent. The filtrates containing product were concentrated to give 1.9 g (57%) of 4-[[4-(2-chlorophenyl)-9-methyl-6H-thieno[3,2-f][1,2,4]triazolo[4,3a][1,4]diazepin-2-yl]ethynyl]-2-(ethoxycarbonyl)benzeneacetic acid diethyl ester. The analytical sample was prepared by recrystallization from ethyl acetate and obtained as pale yellow prisms: mp 80–83° C.

EXAMPLE 2

4-[2-[4-(2-Chlorophenyl)-9-methyl-6H-thieno[3,2-f][1,2,4]triazolo[4,3-a][1,4]diazepin-2-yl]ethyl]-2(ethoxycarbonyl)benzeneacetic acid A mixture of 1.9 g (3.3 mmol) of 4-[[4-(2-chlorophenyl)-9-methyl-6H-thieno[3,2-f][1,2,4]triazolo[4-,3a][1,4]diazepin-2-yl]ethynyl]-2-(ethoxycarbonyl)benzeneacetic acid diethyl ester, 140 mL of ethanol, 60 mL of THF, and 1 g of 5% Pd/C was hydrogenated at atmospheric pressure for 22 hours. The catalyst was removed by filtration and the filtrates concentrated to give 1.9 g (100%) of the crude diester. A solution of 1.1 g (1.9 mmol) of diester, 1.95 mL of 1N NaOH, 40 mL of ethanol, and 10 mL of H2O was stirred under nitrogen for 16 hours. An additional 1.4 mL of 1N NaOH was added and the mixture heated at 45° C. for 4 hours. A few drops of acetic acid was added and the ethanol was removed in vacuo. The residue was partitioned between ethyl acetate and dilute $NH_4OH$. The aqueous phase was acidified with acetic acid and extracted with $CH_2Cl_2$. The organic phases were dried and concentrated. The residue was purified by thick layer chromatography using ethyl acetate/CH3OH (3:1) containing a few drops of $NH_4OH$ as the eluent. The plates were redeveloped in the same solvent mixture containing a few drops of acetic acid. The product was removed and crystallized from ethyl acetate to give 0.6 g (33%) of 4-[2-[4-(2-chlorophenyl)-9-methyl-6H-thieno[3,2-f][1,2,4]triazolo[4,3-a][1,4]diazepin-2-yl]ethyl]-2-(ethoxycarbonyl)benzeneacetic acid as pale yellow prisms: mp 128–132° C.

EXAMPLE 3

(E)-5-[2-[4-(2-Chlorophenyl)-9-methyl-6H-thieno[3,2-f-][1,2,4]triazolo[4,3-a][1,4]diazepin-2-yl]ethyl]-2-[2-[3[2-(4-cyclobutyl-2-thiazolyl)ethenyl]phenylamino]-2-oxoethyl]-benzoic acid ethyl ester A mixture of 0.3 g (0.55 mmol) of 4-[2-[4-(2-chlorophenyl)-9-methyl-6H-thieno[3,2-f][1,2,4]triazolo[4,3-a][1,4]diazepin-2-yl]ethyl]2-(ethoxycarbonyl)benzeneacetic acid, 0.17 g (0.66 mmol) of (E)-3[2-[4-(cyclobutyl)-2-thiaxolyl]ethenyl]benzeneamine, 0.13 g (0.66 mmol) of N-ethyl-N'-(3-dimethylaminopropyl)carbodiimide hydrochloride, 0.11 g (0.87 mmol) of 4-dimethylaminopyridine, and 45 mL of $CH_2Cl_2$ was stirred under nitrogen for 3 days. The reaction was washed with dilute $NH_4OH$, which was extracted with $CH_2Cl_2$. The organic phases were combined, dried and concentrated. The residue was filtered through a small amount of silica gel using ethyl acetate, diethyl ether, and finally ethyl acetate/ethanol (15:1) as the eluents. The fractions containing the product were combined and concentrated. The residue was crystallized from ethyl acetate to give 0.2 g (46%) of (E)-5-[2-[4-(2-chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]phenylamino]-2-oxoethyl]-benzoic acid ethyl ester as a colorless powder, mp 118–120° C.

EXAMPLE 4

(E)-5-[2-[4-(2-Chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]phenylamino]-2oxoethyl]-benzoic acid monohydrate A solution of 0.2 g (0.25 mmol) of (E)-5-[2-[4-(2-chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]phenylamino]-2-oxoethyl]-benzoic acid ethyl ester, 4 mL of 1N NaOH, 11 mL of $H_2O$, and 15 mL of ethanol was stirred for 40 hours and acidified with acetic acid. The product was extracted with $CH_2Cl_2$, which was dried and concentrated. The residue was chromatographed on silica gel using ethyl acetate/ethanol (10:1) followed by the same mixture (4:1) as the eluent. The fractions containing the product were concentrated and the residue triturated with ether/pet. ether and filtered to give 0.12 g (61%) of (E)-5-[2-[4-(2-chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl )ethenyl]phenylamino]-2-oxoethyl]-benzoic acid monohydrate as an off-white powder: mp 143–148° C.

EXAMPLE 5

(E)-4-[2-[4-(2-Chlorophenyl)-9-methyl-6H-thieno-[3,2-f][1,2,4]triazolo[4,3-a][1,4]diazepin-2-yl]ethyl]-N-[3-[2-(4-cyclobutyl-2-thiazolyl)ethenyl]phenyl]-2-[2-propenylamino)-carbonyl]benzeneacetamide A mixture of 0.1 g (0.13 mmol) of (E)-5-t2-[4-(2-chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]phenylamino]-2-oxoethyl]-benzoic acid monohydrate, 0.03 g (0.16 mmol) of N-ethyl-N'-(3-dimethylaminopropyl)-carbodiimide hydrochloride, 0.02 mL (4 mmol) of allylamine and 15 mL of dry $CH_2Cl_2$ was stirred at room temperature under nitrogen for 18 hours and concentrated to dryness. The residue was purified by thick layer chromatography using ethyl acetate/$CH_3OH$ (5:1) as the eluent. The product was isolated and partitioned between $CH_2Cl_2$ and dilute $NH_4OH$. The organic phases were concentrated and the residue triturated with hot ethyl acetate and filtered. The filtrates were concentrated and the solid triturated with diethyl ether and filtered to give 60 mg (57%) of (E)-4-[2-[4-(2-Chlorophenyl)-9-methyl-6H-thieno-[3,2-f][1,2,4]triazolo[4,3-a][1,4 ]-diazepin-2-yl]ethyl]-N-[3-[2-( 4-cyclobutyl-2-thiazolyl)ethenyl]-phenyl]-2-[2-propenylamino)carbonyl]benzeneacetamide as a tan powder: mp 127–132° C.

EXAMPLE 6

Tablet Formulation (Wet Granulation)

| Item | Ingredient | mg/tablet | | |
|------|-----------|-----------|-----|-----|
| | | 25 mg | 100 mg | 500 mg |
| 1 | (E)-5-[2-[4-(2-Chlorophenyl)-9-methyl-6H-thieno-[3,2-f][1,2,4]triazolo[4,3-a][1.4)diazepin-2-yl]ethyl]-2-[2-[3-[2-(4-cyclobutyl-2-thiazolyl)ethenyl]phenylamino]-2-oxoethyl]-benzoic acid monohydrate | 25 | 100 | 500 |
| 2. | Lactose Anhydrous DTG | 105 | 30 | 150 |
| 3. | Pregelatinized Starch | 6 | 6 | 30 |
| 4. | Microcrystalline Cellulose | 30 | 30 | 150 |
| 5. | Magnesium Stearate | 1 | 1 | 5 |
| | TOTAL | 167 | 167 | 835 |

Preparation of Tablets:
1. Mix items 1, 2, 3 and 4 and granulated with water.
2. Dry the granulation at 50° C.
3. Pass the granulation through a suitable milling equipment
4. Add Item 5 and mix for three minutes; compress on a suitable press.

EXAMPLE 7

Capsule Formulation (Wet Granulation)

| Item | Ingredient | mg/tablet | | |
|------|-----------|-----------|-----|-----|
| | | 25 mg | 100 mg | 500 mg |
| 1 | (E)-5-[2-[4-(2-Chlorophenyl)-9-methyl-6H-thieno-[3,2-f][1,2,4]triazolo[4,3-a][1,4]diazepin-2-yl]ethyl]-2-[2-[3-[2-(4-cyclobutyl-2-thiazolyl)ethenyl]phenylamino]-2-oxoethyl]-benzoic acid monohydrate | 25 | 100 | 500 |
| 2. | Lactose Hydrous | 123 | 148 | — |
| 3. | Corn Starch | 35 | 40 | 70 |
| 4. | Talc | 15 | 10 | 25 |
| 5. | Magnesium Stearate | 2 | 2 | 5 |
| | TOTAL | 200 | 300 | 600 |

Preparation of Capsules:
1. Mix items 1, 2 and 3 in a suitable mixer for 30 minutes.
2. Add items 4 and 5 and mix for 3 minutes.
3. Fill into a suitable capsule.

EXAMPLE 8

Tablet Formulation (Wet Granulation)

| Item | Ingredient | mg/tablet | | |
|------|-----------|-----------|-----|-----|
| | | 25 mg | 100 mg | 500 mg |
| 1 | (E)-5-[2-[4-(2-Chlorophenyl)-9-methyl-,6H-thieno-[3,2-f][1,2,4]triazolo[4,3-a][1,4]diazepin-2-yl]ethyl]-N-[3-[2-(4-cyclobutyl-2-thiazolyl)ethenyl]phenyl]-2-[2-propenylamino]-carbonyl]benzeneacetamide | 25 | 100 | 500 |
| 2. | Lactose Anhydrous DTG | 105 | 30 | 150 |
| 3. | Pregelatinized Starch | 6 | 6 | 30 |
| 4. | Microcrystalline Cellulose | 30 | 30 | 150 |
| 5. | Magnesium Stearate | 1 | 1 | 5 |
| | TOTAL | 167 | 167 | 835 |

Preparation of Tablets:
1. Mix items 1, 2, 3 and 4 and granulated with water.
2. Dry the granulation at 50° C.
3. Pass the granulation through a suitable milling equipment
4. Add Item 5 and mix for three minutes; compress on a suitable press.

EXAMPLE 9

Capsule Formulation (Wet Granulation)

| Item | Ingredient | mg/tablet | | |
|---|---|---|---|---|
| | | 25 mg | 100 mg | 500 mg |
| 1 | (E)-5-[2-[4-(2-Chlorophenyl)-9-methyl-6H-thieno-[3,2-f][1,2,4]triazolo[4,3-a][1,4]diazepin-2-yl]ethyl]-N-[3-[2-(4-cyclobutyl-2-thiazolyl)ethenyl]phenyl]-2-[2-propenyl-amino]-carbonyl]benzene-acetamide | 25 | 100 | 500 |
| 2. | Lactose Hydrous | 123 | 148 | — |
| 3. | Corn Starch | 35 | 40 | 70 |
| 4. | Talc | 15 | 10 | 25 |
| 5. | Magnesium Stearate | 2 | 2 | 5 |
| | TOTAL | 200 | 300 | 600 |

Preparation of Capsules:
1. Mix items 1, 2 and 3 in a suitable mixer for 30 minutes.
2. Add items 4 and 5 and mix for 3 minutes.
3. Fill into a suitable capsule.

EXAMPLE 10

Tablet Formulation (Wet Granulation)

| Item | Ingredient | mg/tablet | | |
|---|---|---|---|---|
| | | 25 mg | 100 mg | 500 mg |
| 1 | (E)-5-[2-[4-(2-Chlorophenyl)-9-methyl-6H-thieno-[3,2-f][1.2,4]triazolo[4,3-a][1,4]diazepin-2-yl]-2-[2-[3-[2-(4-cyclobutyl-2-thiazolyl)ethenyl]phenylamino]-2-oxoethyl]benzoic acid ethyl ester | 25 | 100 | 500 |
| 2. | Lactose Anhydrous DTG | 105 | 30 | 150 |
| 3. | Pregelatinized Starch | 6 | 6 | 30 |
| 4. | Microcrystalline Cellulose | 30 | 30 | 150 |
| 5. | Magnesium Stearate | 1 | 1 | 5 |
| | TOTAL | 167 | 167 | 835 |

Preparation of Tablets:
1. Mix items 1, 2, 3 and 4 and granulated with water.
2. Dry the granulation at 50° C.
3. Pass the granulation through a suitable milling equipment
4. Add Item 5 and mix for three minutes; compress on a suitable press.

EXAMPLE 11

Capsule Formulation (Wet Granulation)

| Item | Ingredient | mg/tablet | | |
|---|---|---|---|---|
| | | 25 mg | 100 mg | 500 mg |
| 1 | (E)-5-[2-[4-(2-Chlorophenyl)-9-methyl-6H-thieno-[3,2-f][1,2,4]triazolo[4,3-a][1,4]diazepin-2-yl]-2-[2-[3-[2-(4-cyclobutyl-2-thiazolyl)ethenyl]phenylamino]-2-oxoethyl]benzoic acid ethyl ester | 25 | 100 | 500 |

-continued

| Item | Ingredient | mg/tablet | | |
|---|---|---|---|---|
| | | 25 mg | 100 mg | 500 mg |
| 2. | Lactose Hydrous | 123 | 148 | — |
| 3. | Corn Starch | 35 | 40 | 70 |
| 4. | Talc | 15 | 10 | 25 |
| 5. | Magnesium Stearate | 2 | 2 | 5 |
| | TOTAL | 200 | 300 | 600 |

Preparation of Capsules:
1. Mix items 1, 2 and 3 in a suitable mixer for 30 minutes.
2. Add items 4 and 5 and mix for 3 minutes.
3. Fill into a suitable capsule.

We claim:
1. A compound of formula:

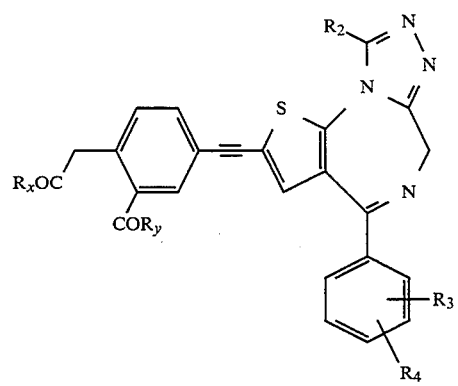

wherein $R_x$ and $R_y$ are independently lower alkoxy, $R_2$ is lower alkyl, lower alkoxy or trifluoromethyl and $R_3$ and $R_4$ are independently hydrogen, chlorine, fluorine, lower alkyl or lower alkoxy.

2. A compound of claim 1, wherein $R_2$ is lower alkyl.

3. The compound 4-[[4(2-Chlorophenyl)-9-methyl-6H -thieno[3,2-f][1,2,4]triazolo[4,3a][1,4]diazepin-2-yl]ethynyl]-2-(ethoxycarbonyl)benzeneacetic acid diethyl ester.

4. A compound of formula:

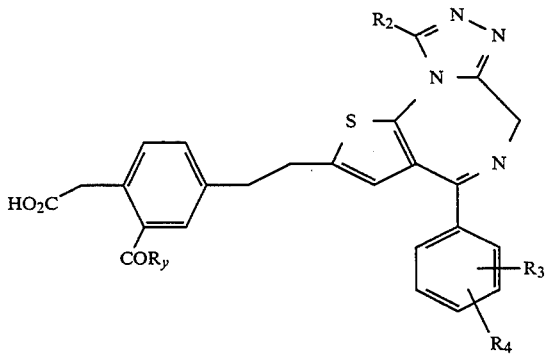

wherein $R_y$ is lower alkoxy, $R_2$ is lower alkyl, lower alkoxy, or trifluoromethyl, and $R_3$ and $R_4$ are independently hydrogen, chlorine, fluorine, lower alkyl or lower alkoxy.

5. A compound of claim 4, wherein $R_2$ is lower alkyl.

6. The compound 4- [2- [4-(2-Chlorophenyl)-9-methyl-6H -thieno[3,2-f][1,2,4]triazolo[4,3-a][1,4]diazepine-2-yl]ethyl]-2-(ethoxycarbonyl)benzeneacetic acid.

* * * * *